(12) United States Patent
Mari

(10) Patent No.: US 11,723,703 B2
(45) Date of Patent: *Aug. 15, 2023

(54) SCREW IMPLANTS FOR BONE FUSION

(71) Applicant: GLOBUS MEDICAL, INC., Audubon, PA (US)

(72) Inventor: Liana Mari, Wynnewood, PA (US)

(73) Assignee: Globus Medical, Inc., Audubon, PA (US)

(*) Notice: Subject to any disclaimer, the term of this patent is extended or adjusted under 35 U.S.C. 154(b) by 160 days.

This patent is subject to a terminal disclaimer.

(21) Appl. No.: 17/182,453

(22) Filed: Feb. 23, 2021

(65) Prior Publication Data

US 2021/0251672 A1 Aug. 19, 2021

Related U.S. Application Data

(63) Continuation of application No. 16/112,838, filed on Aug. 27, 2018, now Pat. No. 10,925,653, which is a continuation-in-part of application No. 15/795,920, filed on Oct. 27, 2017, now Pat. No. 10,335,216, which is a continuation-in-part of application No. 14/563,697, filed on Dec. 8, 2014, now abandoned, which is a continuation of application No. 13/184,026, filed on Jul. 15, 2011, now abandoned.

(51) Int. Cl.
*A61B 17/86* (2006.01)
*A61B 17/70* (2006.01)
*A61F 2/30* (2006.01)

(52) U.S. Cl.
CPC ...... *A61B 17/8685* (2013.01); *A61B 17/7055* (2013.01); *A61B 17/863* (2013.01); *A61B 17/8695* (2013.01); *A61B 17/866* (2013.01); *A61F 2002/30995* (2013.01)

(58) Field of Classification Search
CPC . A61B 17/86; A61B 17/8605; A61B 17/8625; A61B 17/863; A61B 17/8635; A61B 17/8685; A61B 17/8695
See application file for complete search history.

(56) References Cited

U.S. PATENT DOCUMENTS

| 4,175,555 A | 11/1979 | Herbert |
| 4,463,753 A | 8/1984 | Gustilo |
| 4,569,338 A | 2/1986 | Edwards |

(Continued)

FOREIGN PATENT DOCUMENTS

| JP | 2003-526456 A | 9/2003 |
| WO | 9002526 A1 | 3/1990 |
| WO | 2004086991 A1 | 10/2004 |

*Primary Examiner* — Si Ming Ku

(57) ABSTRACT

Systems, apparatuses and methods for bone fusion are disclosed. In particular, a fixation screw assembly is provided that comprises a bone engagement portion including a shaft and a head member. The assembly also includes a flexible washer member that can be operably attached and secured around the head member of the bone engagement portion. The washer member is polyaxial relative to the bone engagement portion, such that it can assume a variety of angles. The washer member can help prevent back out of the bone engagement portion when the bone engagement portion is implanted into a bone member. The design of the fixation screw assembly can be used in different fusion procedures, including fusion of the sacroiliac joint.

19 Claims, 12 Drawing Sheets

(56) References Cited

U.S. PATENT DOCUMENTS

| | | |
|---|---|---|
| 5,019,079 A | 5/1991 | Ross |
| 5,334,205 A | 8/1994 | Cain |
| D368,777 S | 4/1996 | Goble et al. |
| 5,593,407 A | 1/1997 | Reis |
| 5,601,553 A | 2/1997 | Trebing et al. |
| 5,643,264 A | 7/1997 | Sherman |
| 5,871,486 A | 2/1999 | Huebner et al. |
| 5,964,768 A | 10/1999 | Huebner |
| 6,019,760 A | 2/2000 | Metz-Stavenhagen et al. |
| 6,030,162 A | 2/2000 | Huebner |
| 7,608,077 B2 | 10/2009 | Cragg et al. |
| 7,615,069 B2 | 11/2009 | Paul |
| 8,162,998 B2 | 4/2012 | Schlienger et al. |
| 8,641,733 B2 | 2/2014 | Chin et al. |
| 8,808,339 B2 | 8/2014 | Varela et al. |
| 8,894,685 B2 | 11/2014 | Mickiewicz et al. |
| 8,998,968 B1 | 4/2015 | Brow |
| 9,005,184 B2 * | 4/2015 | Mayer .................... A61B 5/076 |
| | | 606/154 |
| 9,044,277 B2 | 6/2015 | O'Neil et al. |
| 9,119,678 B2 | 9/2015 | Duggal et al. |
| 9,717,538 B2 | 8/2017 | Chin et al. |
| 2005/0101961 A1 | 5/2005 | Huebner et al. |
| 2007/0233123 A1 | 10/2007 | Ahmad et al. |
| 2008/0255622 A1 | 10/2008 | Mickiewicz et al. |
| 2008/0306555 A1 | 12/2008 | Patterson et al. |
| 2009/0192551 A1 * | 7/2009 | Cianfrani ............. A61B 17/863 |
| | | 606/301 |
| 2009/0259261 A1 | 10/2009 | Reiley |
| 2011/0045437 A1 * | 2/2011 | Arni .................... A61C 8/0022 |
| | | 433/215 |
| 2011/0087294 A1 | 4/2011 | Reiley |
| 2011/0087296 A1 | 4/2011 | Reiley et al. |
| 2011/0182693 A1 | 7/2011 | Helgerson |
| 2011/0184519 A1 | 7/2011 | Trieu |
| 2011/0213423 A1 | 9/2011 | Biedermann et al. |
| 2011/0313472 A1 | 12/2011 | Yap et al. |
| 2012/0156647 A1 | 6/2012 | Yoon et al. |
| 2016/0310188 A1 | 10/2016 | Marino et al. |
| 2017/0196608 A1 | 7/2017 | Castaneda et al. |
| 2017/0296246 A1 * | 10/2017 | Huang ................... A61L 31/18 |
| 2018/0042652 A1 | 2/2018 | Mari et al. |

\* cited by examiner

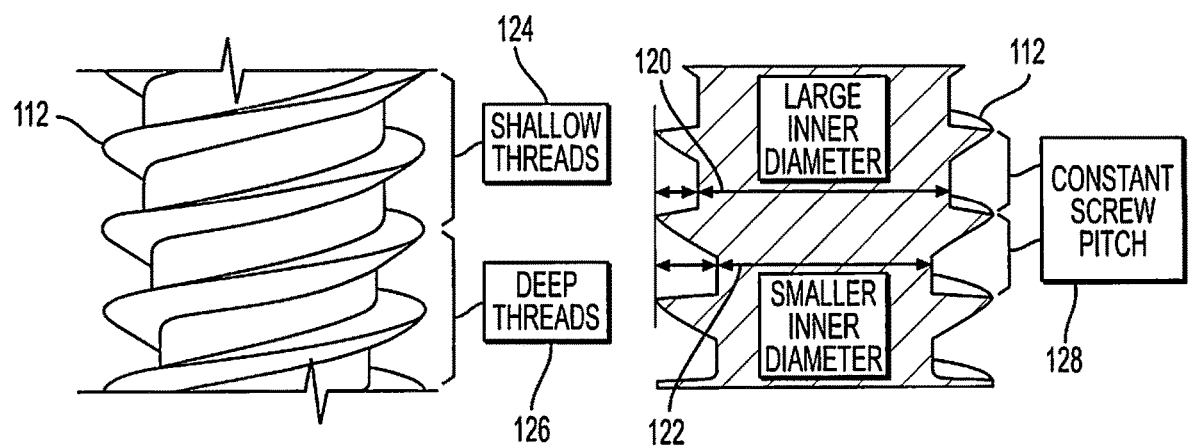
FIG. 7C  FIG. 7D
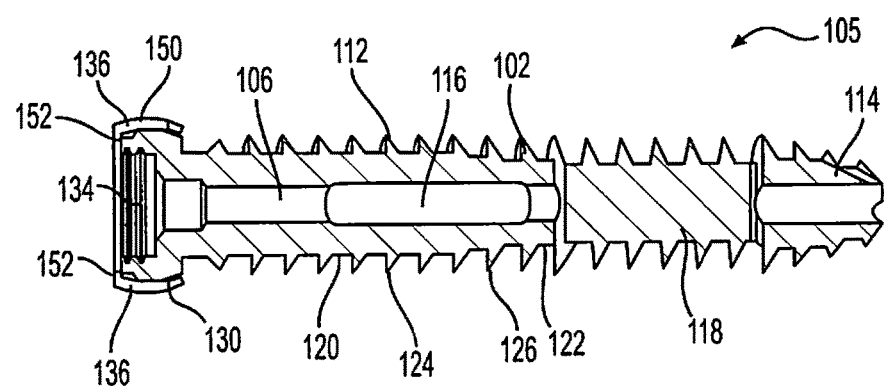
FIG. 7E

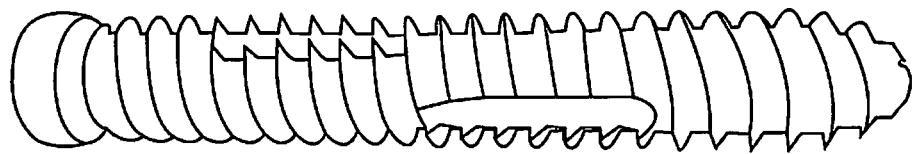
FIG. 10
  
FIG. 11A  FIG. 11B  FIG. 11C
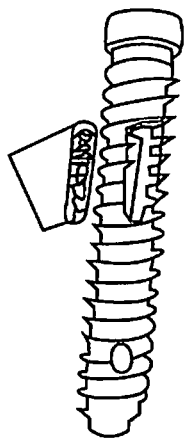 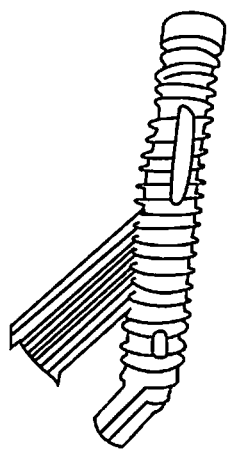 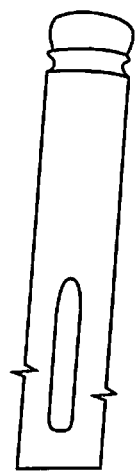
FIG. 11D  FIG. 11E  FIG. 11F

SCREW IMPLANTS FOR BONE FUSION

CROSS-REFERENCE TO RELATED APPLICATIONS

This Patent Application is a continuation of U.S. patent application Ser. No. 16/112,838 filed on Aug. 27, 2018, which is a continuation-in-part of U.S. patent application Ser. No. 15/795,920 filed on Oct. 27, 2017, which is a continuation-in-part of U.S. patent application Ser. No. 14/563,697, filed Dec. 8, 2014, which is a continuation application of U.S. patent application Ser. No. 13/184,026, filed on Jul. 15, 2011, now abandoned, all of which are herein incorporated by reference in their entireties for all purposes.

FIELD OF THE INVENTION

The present application generally relates to fixation implants, and in particular, screw implants.

BACKGROUND OF THE INVENTION

In vertebrate anatomy, the sacrum is a large, triangular bone that lies at the bottom of the lumbar spine, where it connects with the L5 vertebra. The sacrum lies adjacent to two hip bones, known as the right ilium and left ilium. The sacrum connects with these bones via joints known as sacroiliac joints (or SI joints).

The sacroiliac joints assist in the transmission of forces from the spine to the lower extremities. Degeneration of the sacroiliac joints can occur due to diseases, such as degenerative sacroiliitis and inflammatory sacroiliitis, as well as due to normal aging and trauma. One type of treatment for a degenerated sacroiliac joint is fusion of the joint, which ultimately relieves pain.

Thus, there remains a need for improved implants that assist in the fusion of sacroiliac joints.

SUMMARY OF THE INVENTION

Various fixation implants are provided for assisting in bone fusion. In some embodiments, an implant for implanting across a sacroiliac joint is provided. The implant includes a bone engaging portion comprising a shaft and a head portion, wherein the shaft includes a plurality of threads. The shaft includes a biomaterial window for receiving biological material to assist in fusion of the sacroiliac joint. The implant further includes a flexible washer member configured to be in a locking configuration around the head portion, wherein the washer member includes a plurality of slits that accommodate expansion of the washer member around the head portion and one or more engagement members for engaging a bone surface. The washer member is capable of polyaxial movement relative to a longitudinal axis of the bone engaging portion.

In some embodiments, an implant for implant across a sacroiliac joint comprises a bone engaging portion comprising a shaft and a head portion, wherein the shaft includes a plurality of threads. The shaft can have a length of between about 25 mm and 110 mm for extending across at least a portion of an ilium, a sacroiliac joint and sacrum. The implant further includes a flexible washer member configured to be in a locking configuration around the head portion. The washer member is capable of expansion around the head portion and includes one or more engagement members for engaging a bone surface. The washer member is capable of polyaxial movement relative to a longitudinal axis of the bone engagement portion.

According to some embodiments, a fixation screw assembly for fusing a sacroiliac joint includes a fixation member and a washer member. The fixation member includes a head member and a bone-engaging portion coupled to the head member. The head member having a generally spherical outer surface and a groove. The washer member has an inner annular lip. The washer member is operatively coupled to the fixation member around the head member. An inner surface of the washer member is generally spherical and corresponding to the generally spherical outer surface of the head member. The washer member is capable of polyaxial movement relative to a longitudinal axis of the fixation member. When the washer member is sufficiently angled relative to the longitudinal axis of the fixation member, the lip of the washer member bottoms out on the groove of the head member.

According to yet other embodiments, a fixation screw assembly for fusing a sacroiliac joint includes a fixation member and a washer member. The fixation member includes a head member and a bone-engaging portion including a plurality of threads coupled to the head member. The head member has a generally spherical outer surface. The bone-engaging portion includes a dual inner diameter including a first portion with shallow threads and a second portion with deep threads. The washer member is operatively coupled to the fixation member around the head member. An inner surface of the washer member is generally spherical and corresponds to the generally spherical outer surface of the head member. The washer member is capable of polyaxial movement relative to a longitudinal axis of the fixation member.

In some embodiments, a method of fusing a sacroiliac joint is provided. The method comprises forming an incision in a patient; delivering a fixation screw assembly through the incision and laterally toward an ilium, wherein the fixation screw assembly includes a washer member and a bone engagement portion comprising a shaft and head member, wherein the washer member is operatively coupled to the bone engagement portion around the head member, and wherein the washer member is capable of polyaxial movement relative to a longitudinal axis of the bone engagement portion; driving the fixation screw assembly through the ilium, across a sacroiliac joint and into a sacrum until the washer member engages a surface of the ilium; and maintaining the fixation screw assembly in place to assist in fusion of the sacroiliac joint.

BRIEF DESCRIPTION OF THE DRAWINGS

FIGS. 7A-7F illustrate various view of an alternative embodiment of a fixation screw assembly.

FIG. 10 illustrates a screw assembly with an acid etching treatment.

FIGS. 11A-11F illustrates screw assemblies manufactured by various methods.

DETAILED DESCRIPTION OF THE ILLUSTRATED EMBODIMENTS

Detailed embodiments of the invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

The present application generally relates to fixation implants, and in particular, screw implants. The screw implants can be used to assist in the fusion of the sacroiliac joint. In some embodiments, the screw implants can be introduced through an ilium, past a degenerated sacroiliac joint and into the sacrum. After implantation, the screw implants remain in place and assist in the fusion of the sacroiliac joint.

One of the difficulties with implanting a screw into a bone member is inadvertent back out. For the ilia, which are wing-shaped, the inadvertent back out of fixation screws presents a challenging problem due to the curved surfaces. To address this problem, the screw implants of the present application advantageously provide a mechanism that prevents or reduces the risk of inadvertent back out from an ilium. In particular, the screw implants include an easily assembled washer member that assists in preventing inadvertent back out of the screw implant. The washer member is advantageously designed to have flexibility to conform to the ilium contour when the screw implant is implanted in the ilium.

Figure 1A:
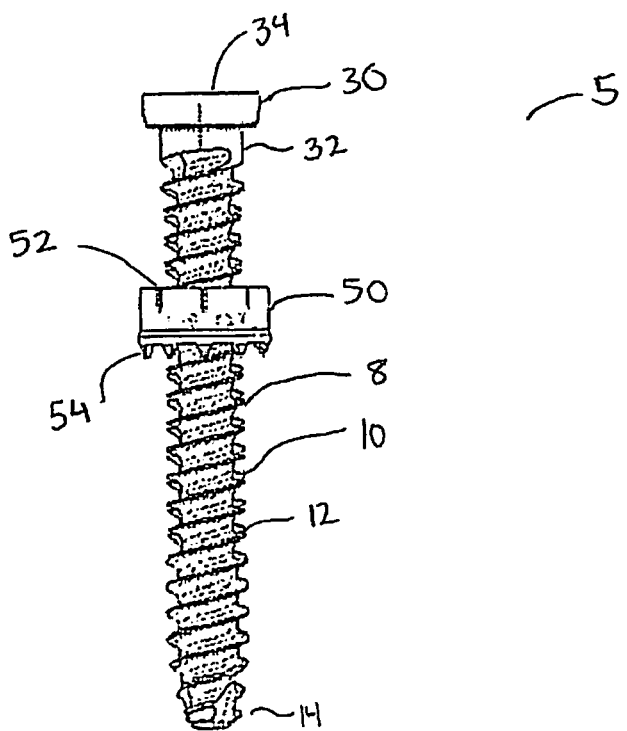
FIG. 1A is a front view of a fixation screw assembly for sacroiliac joint fusion according to some embodiments.

FIG. 1A is a front view of a fixation screw assembly for sacroiliac joint fusion according to some embodiments. The fixation screw assembly 5 includes a bone-engaging portion 8 comprising a shaft 10 operably coupled to a head member 30. The fixation screw assembly 5 also includes a washer member 50 that can be upwardly loaded via the shaft 10 until it is positioned proximate the head member 30. Once proximate the head member 30, the washer member 50 can be forced upwardly (e.g., using an instrument) around the head member 30, where it is placed into a locked configuration in which it is securely fastened around the head member 30. Once in the locked configuration, the fixation screw assembly 5 can be inserted into a bone member, such as an ilium, whereby it can assist in fusion (e.g., of the sacroiliac joint).

The shaft 10 of the bone-engaging portion 8 includes a plurality of threads 12. As shown in FIG. 1A, the threads 12 extend along at least a majority of the length of the shaft 10. In other embodiments, the threads 12 extend only along a minority portion of the shaft 10. In some embodiments, the threads 12 of the bone-engaging portion 8 of the shaft 10 are dual lead threads, although any type of thread may be used to facilitate the insertion of bone-engaging portion 8 into bone.

The shaft 10 of the bone-engaging portion 8 also includes a distal portion 14 which serves as the lead end for entry into a bone member. The distal portion 14 can be tapered to assist in the insertion process. In addition, at least one flute can be provided on the distal portion 14 or along any other part of the bone-engaging portion 8 in order to clear any chips, dust, or debris generated when the bone-engaging portion 8 is implanted into bone tissue. In addition, in some embodiments, the shaft 10 can be cannulated to receive a guide wire or other type of instrument to assist in implantation.

Figure 1B:
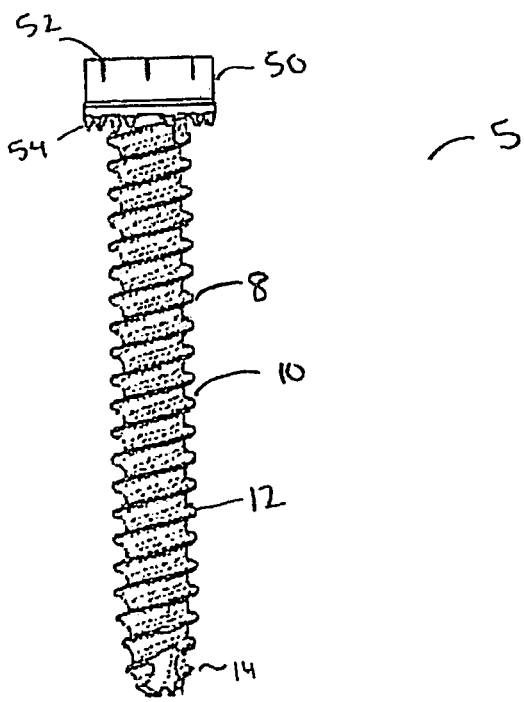
FIG. 1B is a front view of the fixation screw assembly in FIG. 1A with a washer in a locked configuration according to some embodiments.

In some embodiments, the shaft 10 of the fixation screw assembly 5 is inserted through multiple bone members (e.g., through an ilium and sacrum) to assist in fusion. In order to accommodate insertion through multiple bone members, the shaft 10 advantageously has a length of between about 20 mm to about 110 mm, or between about 25 mm to about 110 mm. In some embodiments, the shaft 10 of the fixation screw assembly 5 also has a diameter or width of between about 6 mm and about 14 mm, or between about 8 mm and 12 mm. These ranges advantageously allow biologic material to be packed within the interior of the shaft 10, as discussed in more detail below. As shown in FIGS. 1A and 1B, the shaft 10 of the fixation screw assembly 5 can remain generally constant in diameter along a majority of the length of the assembly 5, thereby advantageously allowing for optimal screw positioning when the bone screw is inserted into a predetermined area in bone tissue. However, in other embodiments, the shaft 10 can taper, such that its diameter becomes narrower towards a distal end of the shaft 10.

The shaft 10 is operably connected to a head member 30. The shaft 10 transitions into the head member 30 via a neck portion 32. In some embodiments, the neck portion 32 has a diameter or width equal to or less than that of the shaft. Within a top portion 34 of the head member 30 is an engagement portion configured to receive a driving instrument, such as a screw driver (not shown). The screw driver can be used to drive the fixation screw assembly 5 into one or more bone members, such as the ilium and/or sacrum.

The fixation screw assembly 5 includes a washer member 50 that is easily assembled into a locked configuration with the bone-engaging portion 8. In some embodiments, the washer member 50 resembles a ring-shaped or annular collar having a circular hole that can fit around the shaft 10 of the fixation screw assembly 5. The washer member 50 can be slidably moved up and down the shaft 10 until it is locked around the head member 30. The washer member 50 includes one or more slits 52 that can accommodate expansion of the washer member 50 over the head member 30, thereby placing the washer member 50 in an assembled and locked configuration around the head member 30. In some embodiments, the washer member 50 is pre-assembled in a locked configuration around the head member 30 of the fixation screw assembly 5 (as shown in FIG. 1B). On an end of the washer member 50 opposite from the slits 52, the washer member 50 includes one or more engagement surfaces or teeth 54 that can engage a surface of a bone member (e.g., an ilium) when the fixation screw assembly 5 is implanted into bone.

Figure 2:
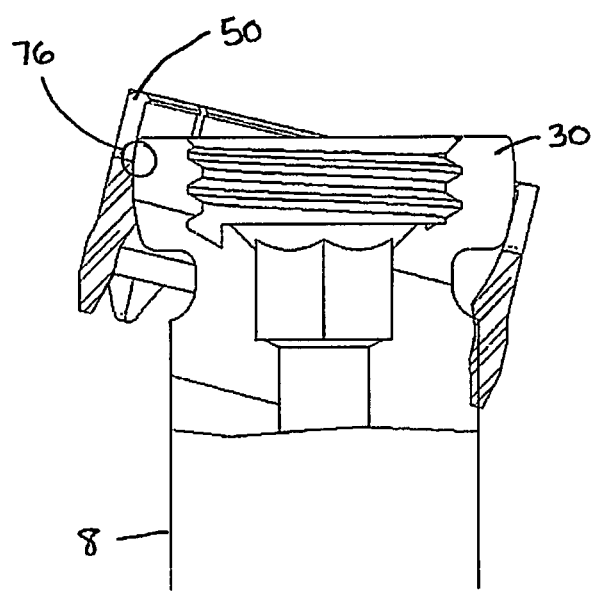
FIG. 2 is a close-up cross-sectional view of a washer member angled relative to the bone-engaging portion according some embodiments.

Advantageously, the washer member 50 is flexible and polyaxial relative to the bone-engaging portion 8. In other words, the washer member 50 can be angled, rotated or swiveled in multiple directions, as best shown in FIG. 2. In some embodiments, the washer member 50 can have a central axis that is positioned at an angle of between about 0 and about 30 degrees, or between about 0 and 24 degrees, relative to the longitudinal axis of the bone-engaging portion 8.

The components of the fixation screw assembly 5 can be composed of various biocompatible materials. The materials include, but are not limited to, stainless steel, alloys, titanium, titanium based alloys or polymeric materials.

Figure 6:
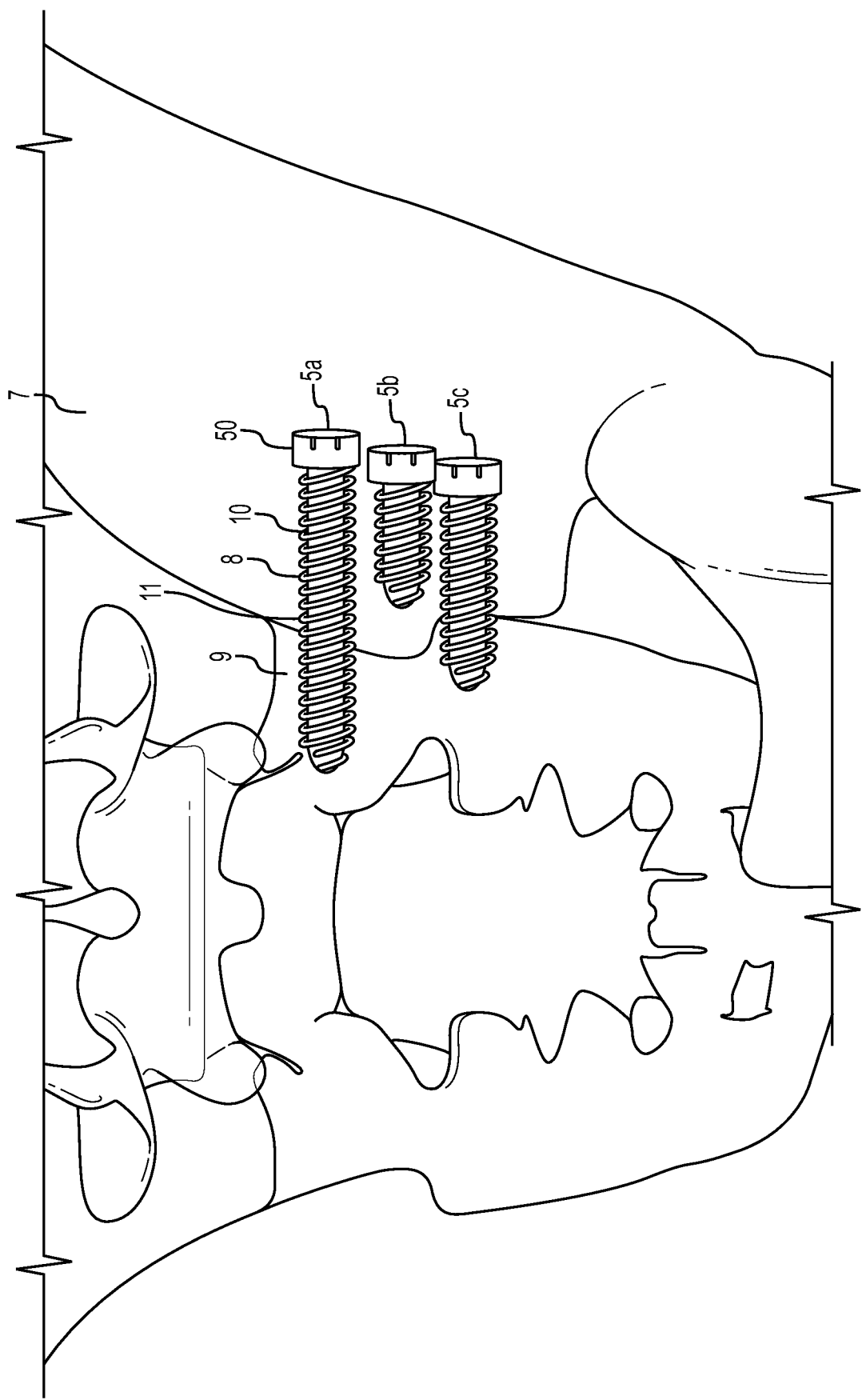
FIG. 6 illustrates multiple fixation screw assemblies assisting in fusion of the sacroiliac joint according to some embodiments.

In operation, when a lateral compressive force is applied to the fixation screw assembly 5, the bone-engaging portion 8 is driven through a bone member, such as the ilium. As the bone-engaging portion 8 is driven laterally, the washer member 50 also engages a surface of the bone member (as shown in FIG. 6). The washer member 50 can engage the bone member at a different angle from the bone-engaging portion 8. This relative angulation advantageously allows the washer member 50 to engage a curved surface of a bone member (e.g., the ilium) with ease, even when the bone-engaging portion 8 is at a different angle. Furthermore, the compressive force of an angled washer member 50 against the head member 30 of the bone-engaging portion 8 also advantageously prevents back out of an implanted fixation screw assembly 5.

FIG. 2 is a close-up cross-sectional view of a washer member angled relative to the bone-engaging portion according some embodiments. From this view, the angulation of the washer member 50 relative to the head member 30 of the bone-engaging portion 8 is visible. Also, the physical interface 76 between the washer member 50 and the head member 30 is also shown. When a force is applied, the washer member 50 will be placed in a compressive force with the head member 30 at the interface 76, thereby helping to prevent inadvertent back out of the bone-engaging portion 8 from a bone member.

Figure 3:
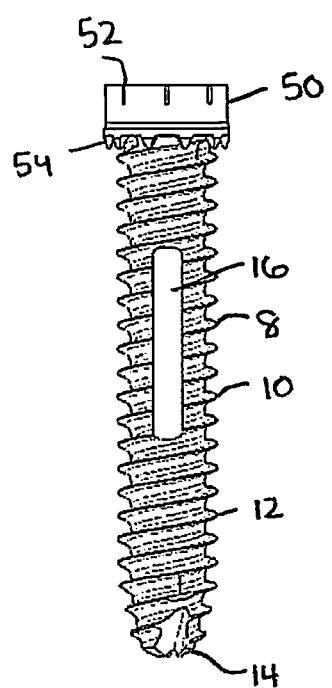
FIG. 3 is a front view of a fixation screw assembly having a biomaterial window according to some embodiments.

FIG. 3 is a front view of a fixation screw assembly having a biomaterial window according to some embodiments. The fixation screw assembly 5 is similar to the assembly in FIGS. 1A and 1B, except that it also includes a biomaterial window 16. Biological material, including natural and synthetic material, can be inserted into the biomaterial window 16 to assist in bone growth and fusion. In some embodiments, the biological material comprises a rectangular window, as shown in the illustrated embodiment. The biomaterial window advantageously has a length of between about ¼ to ⅘ of the length of the shaft 10, such that it can expand across multiple bone members and/or joints if desired. In some embodiments, the biomaterial window has a length of between about ⅓ to ½ of the length of the shaft 10.

Figure 4:
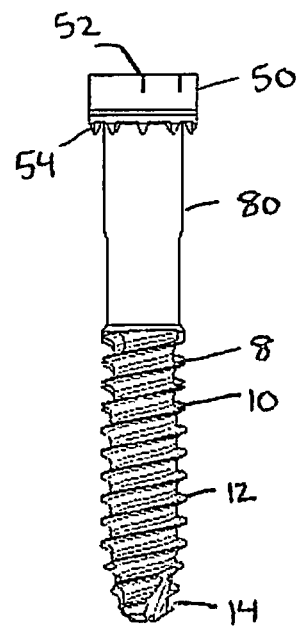
FIG. 4 is a front view of a lag screw assembly for sacroiliac joint fusion according to some embodiments.

FIG. 4 is a front view of a lag screw assembly for sacroiliac joint fusion according to some embodiments. The lag screw assembly 15 includes many of the features of the fixation screw assembly 5 in FIG. 1, including a bone-engaging portion 8, a head portion and a washer 50 configured to lock around the head portion. However, unlike the fixation screw assembly 5, the lag screw assembly 15 further includes a substantially smooth, non-threaded portion 80 that extends between the bone-engaging portion 8 and the head portion. In some embodiments, the threaded portion and the non-threaded portion of the lag screw assembly form a continuous, monolithic component.

Figure 5:
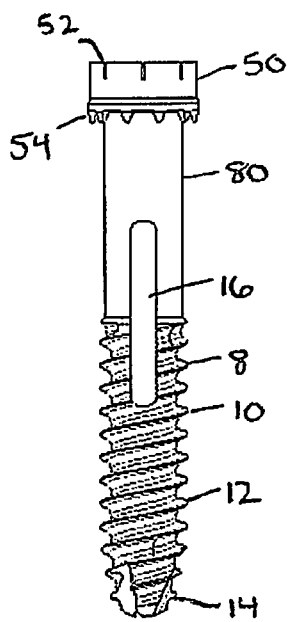
FIG. 5 is a front view of a lag screw assembly having a biomaterial window according to some embodiments.

FIG. 5 is a front view of a lag screw assembly having a biomaterial window according to some embodiments. As shown in the illustrated figure, the lag screw assembly 15 includes a biomaterial window 16 through which biologic material can be deposited. Advantageously, the lag screw assembly 15 can be designed such that the biomaterial window 16 extends across both the threaded portion and the non-threaded portion 80. In other embodiments, the biomaterial window 16 need only extend within the non-threaded portion 80, such that the threads of the lag screw assembly remain intact. However, one skilled in the art will appreciate that the biomaterial window can also extend into the threaded portion of the bone-engaging portion 8 if desired.

FIGS. 7A-7E depict an alternative embodiment of a fixation screw assembly 105 for sacroiliac joint fusion according to other embodiments. Fixation screw assembly 105 is similar to the fixation assemblies previously discussed. Therefore, like features will be described with reference to similar numeral indicators. The fixation screw assembly 105 may be especially suitable as a sacroiliac fusion screw and is intended to increase the fixation achieved in sacroiliac fusion while decreasing the chance of migration. The sacroiliac fixation screw assembly 105 may be placed across the sacroiliac joint, and may traverse varying bone quality, including soft cancellous bone of the sacrum and hard cortical bone of the iliac wings. Oftentimes bone screws do not address the drastic change in bone quality between sacrum and ilium causing haloing of screws on the sacral cancellous side. The fixation screw assembly 105 described herein including a dual inner diameter offers varying thread forms to address varying bone quality. In addition, the screw profile maximizes bone purchase when placed from a cortical to cancellous anatomy. Although generally described with reference to sacroiliac fusion, it will be appreciated that the fixation screw assembly 105 may be utilized for other bone screw applications.

Figure 7A:
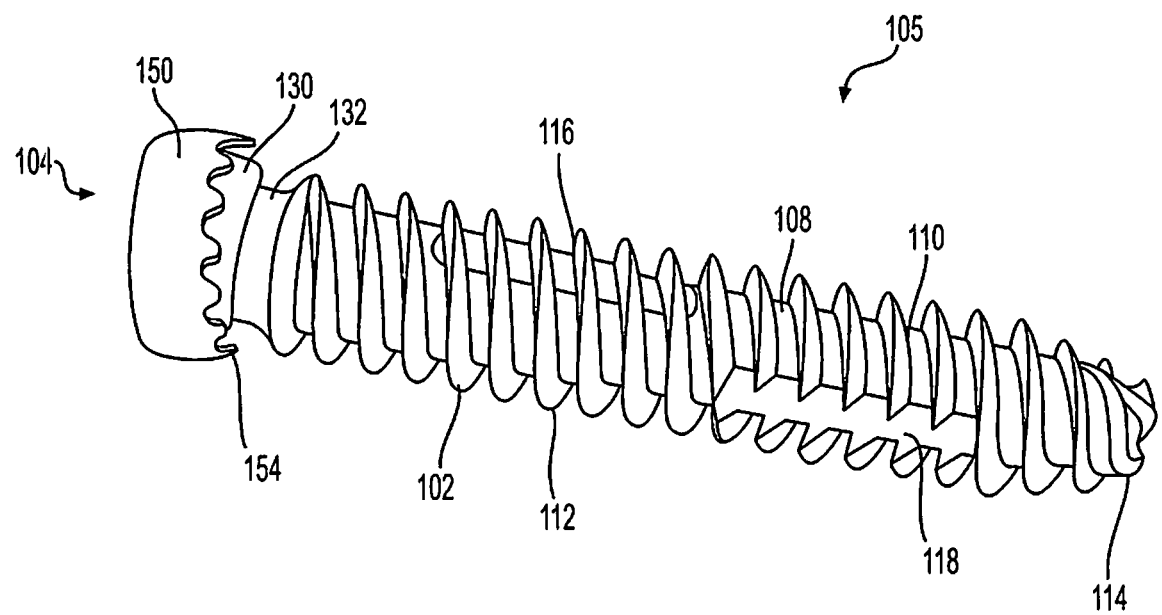
Figure 7B:
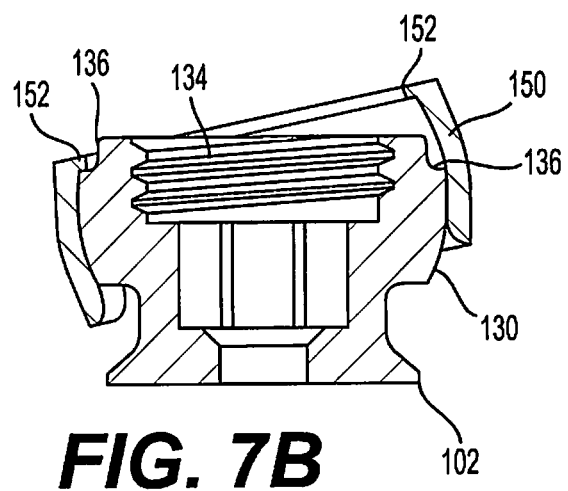

FIG. 7A provides a perspective view of the assembly 105. The fixation screw assembly 105 includes a fixation member 102 and a washer member 150. The fixation member 102 extends from a proximal portion 104 to a distal portion 114. The fixation member 102 includes a bone-engaging portion 108 including a plurality of threads 112. The fixation member 102 comprises a shank or shaft 110 operably coupled to a head member 130, for example, through a neck portion 132. The head member 30 includes an engagement portion 34. The engagement portion 34 may include an internally threaded portion and/or a socket portion (e.g., hexalobular), configured to receive a driving instrument, such as a screw driver (not shown). The screw driver can be used to drive the fixation screw assembly 105 into one or more bone members, such as the ilium and/or sacrum. The hexalobular driving feature may help to prevent stripping of the screw or instrument stripping especially because the fixation member 102 is going through hard cortical bone requiring large forces to drive the screw.

In this embodiment, the shaft 110 is cannulated with an opening 106 extending from the proximal portion 104 to the distal portion 114 of the fixation member 102, and may thereby receive a guide wire or other type of instrument to assist in implantation. When cannulated, the fixation assembly 105 may be inserted in a minimally invasive fashion.

The shaft 110 may include one or more biomaterial slots or windows 116, 118. The biomaterial windows 116, 118 may be filled with bone graft and cross either the sacroiliac joint for fusion or enhance fusion and prevent migration of the screw especially for longer screw lengths. A first biomaterial window 116 is similar to biomaterial window 16 discussed previously. As best seen in the cross-sectional view shown in FIG. 7E, a second biomaterial window 118 is provided closer to the distal portion 114 and is offset 90 degrees relative to the first biomaterial window 116. The biomaterial windows 116, 118 may be elongated having a length extending along the longitudinal axis of the device 102 greater than its respective width. The biomaterial windows 116, 118 are each in fluid communication with the cannulated opening 106. The biomaterial slots or windows 116, 118 may be filled with bone graft material, and are located along the length of the screw to thereby cross the sacroiliac joint for fusion. Additional windows 116, 118 be filled with bone graft to enhance fusion and prevent migration of the device 105 especially for longer screw lengths.

As best seen in the close-up perspective view in FIG. 7C and the close-up cross-sectional view in FIG. 7D, the shaft 110 of the fixation member 102 may include a dual inner diameter. A dual inner diameter screw 102 provides for shallow threads 124 and deep threads 126 with a constant pitch 128 and constant outer diameter on two regions of the bone screw shaft 110. The portion of threads 112 at the proximal portion 104 of the screw 102 (intended to fixate cortical bone) has shallow threads 124 while the portion of threads 112 at the distal tip of the screw 102 (intended to fixate cancellous bone) has deep threads 126. The deep threads 126 combined with the consistency in pitch 128 allow for more bone to be located within the deep threads 126 than within the shallow threads 124, thereby providing increased bone purchase, increased resistance to pullout, and/or increased resistance to migration in softer less dense bone. The dual inner diameter thread may provide for increased fixation, decreased migration, decreased pullout, and decreased haloing of the device 105. This is advantageous when there is a drastic change in bone quality at various parts along the screw length. The feature of varying inner diameter with a constant outer diameter allows for shallow threads 124 at the proximal portion 104 and deep threads 126 at the distal portion 114, which may be ideal for crossing from cortical to cancellous bone.

The fixation screw assembly 105 also includes a washer member 150. The washer member 150 may resemble a ring-shaped or annular collar having a circular hole that can fit around the head member 130 of the fixation screw assembly 105. An inner surface of the washer member 150 may be substantially spherical and may correspond to a substantially spherical outer surface of the head member 130, thereby allowing for polyaxial rotation. Angulation may be needed when the fixation member 102 is implanted laterally because the anatomy of the iliac wings is sloped and may vary drastically between patients.

The washer member 150 may have an inner annular lip 152. As best seen in the close-up cross section shown in FIG. 7B, when the washer member 150 is angled, a portion of the lip 152 on the top of the washer member 150 bottoms out on a groove 136 on the top of the spherical head member 130. The lip 152 on the washer member 150 coupled with the groove 136 on the screw head 130 may allow for maximum angulation while maintaining a portion of the washer member 150 below the equator of the screw shank 110 to prevent disassembly during implantation. Angulation may be important when the sacroiliac screw is implanted laterally to accommodate varying anatomy of the iliac wing. If only minimal angulation were provided by the implant, it is possible that a portion of the washer would not be seated in bone and would be free-floating in soft tissue.

The washer member 150 can be angled, rotated or swiveled in multiple directions. The washer member 150 can be slidably moved up and down the shaft 110 until it is locked around the head member 130. The washer member 150 may include one or more engagement surfaces or teeth 154 that can engage a surface of a bone member (e.g., an ilium) when the fixation screw assembly 1055 is implanted into bone.

The teeth 154 may be provided on the bottom of the washer member 150 to grip into bone and provide tactile feedback to the user. The bottom teeth 154 of the washer member 150 may be tapered inward to allow the teeth 154 of the washer member 150 to recess into bone to provide a lower profile implant and maintain tactile feedback. Similarly, the bottom outside outer surface of the washer member 150 may be tapered inward to allow the teeth 154 of the washer member 150 to sometimes recess into bone to provide a lower profile implant but maintain tactile feedback. The outer diameter of the washer member 150 is larger than the outer diameter of the head member 130 so a portion of the washer teeth 154 always contact bone. The washer member 150 may be assembled onto the fixation member 102 from the top of the fixation member 102 to prevent disassembly of the washer member 150 from the fixation member if the assembly 105 is removed after implantation. In this manner, the washer member 150 cannot disassemble from the screw shank 110 during removal since the washer member 150 is assembled onto the screw shank 110 from the top.

Figure 7F:
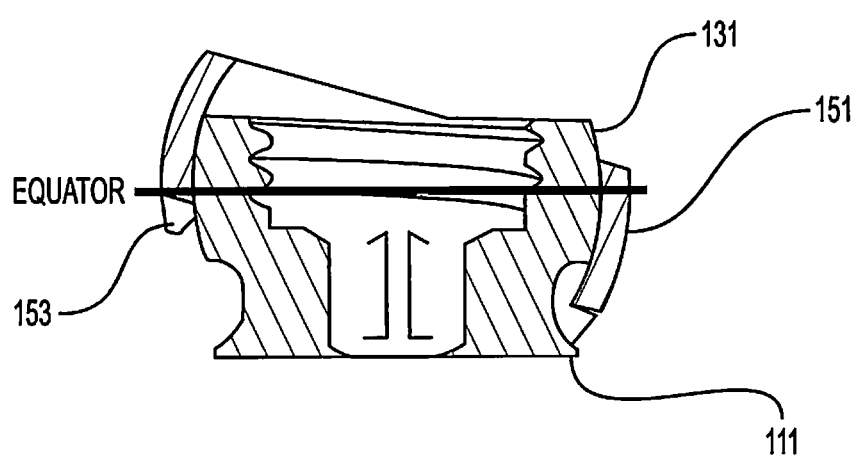

FIG. 7F illustrates another embodiment of a washer member 151 in a cross sectional view. The washer member 151 can be slidably moved up and down the shaft 111 until it is locked around the head member 131. The washer member 151 may include one or more engagement surfaces or teeth 153 that can engage a surface of a bone member (e.g., an ilium) when the fixation screw assembly is implanted into bone. The teeth 153 may be provided on the bottom of the washer member 151 to grip into bone and provide tactile feedback to the user. The bottom teeth 153 of the washer member 150 may be tapered inward to allow the teeth 153 of the washer member 151 to recess into bone to provide a lower profile implant and maintain tactile feedback. Similarly, the bottom outside outer surface of the washer member 151 may be tapered inward to allow the teeth 153 of the washer member 151 to recess into bone to provide a lower profile implant but maintain tactile feedback. The configuration of the washer member 151 allows for extreme angulation. A portion of the washer member is configured to always remain below the equator of the screw head when maximum angulation is achieved to prevent disassembly during implantation. The teeth 153 on the bottom surface of the washer member 151 also provides tactile feedback to the user. The outer diameter of the washer member is larger than the outer diameter of the screw so a portion of the washer teeth 153 always contact bone.

Similar to assembly 105, the components of the fixation screw assembly 105 can be composed of various biocompatible materials. The materials include, but are not limited to, stainless steel, alloys, titanium, titanium based alloys or polymeric materials. The components of the fixation screw assembly 105 can be coated, roughened, or otherwise treated to improve osseointegration. The implant can be driven and inserted by traditional methods, image guided methods, or other using other minimally invasive procedures. The fixation screw assembly 105 may be implanted laterally or posteriorly, for example, to achieve a sacroiliac joint fusion.

Figure 8A:
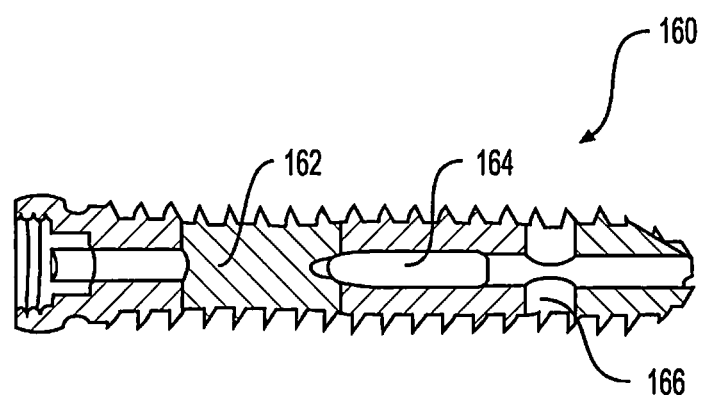
FIGS. 8A and 8B illustrate alternative embodiments of a fixation screw assembly.

In another embodiment as shown in FIG. 8A, the screw assembly 160 may include one or more biomaterial slots or windows 162, 164, 166. The biomaterial windows 162, 164, 166 may be filled with bone graft and cross either the sacroiliac joint for fusion or enhance fusion and prevent migration of the screw especially for longer screw lengths. As best seen in the cross-sectional view shown in FIG. 8A, a second biomaterial window 164 is provided closer to the distal portion and is offset 90 degrees relative to the first biomaterial window 162. A third biomaterial window 166 is provided even closer to the distal end of the shaft and configured to have a smaller diameter than the first and second biomaterial windows. The biomaterial windows 162, 164, 166 may be elongated having a length extending along the longitudinal axis of the device greater than its respective width. The biomaterial windows 162, 164, 166 are each in fluid communication with the cannulated opening. The biomaterial slots or windows 162, 164, 166 may be filled with bone graft material, and are located along the length of the screw to thereby cross the sacroiliac joint for fusion. The biomaterial windows geometry is configured such that there is no gap between adjacent fusion areas. Since the sacroiliac joint is extremely variable in every patient and minimal in width, ensuring the fusion area crosses the joint requires no gap between adjacent fusion areas. In order to not compromise the screws strength, adjacent biomaterial windows are placed perpendicular to each other and are tapered in the overlapping section to maintain as much cross-sectional area as possible.

Figure 8B:
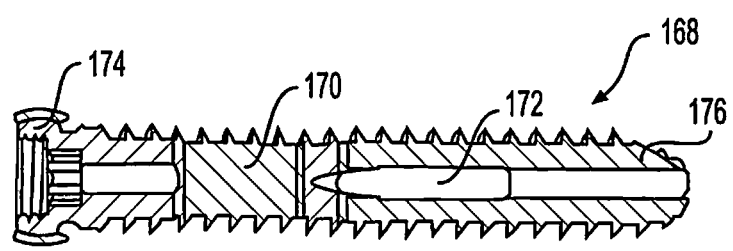
Figure 9A:
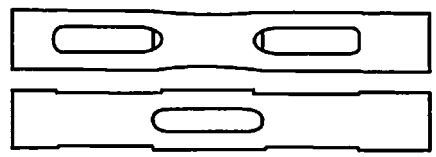
FIGS. 9A-9E illustrates different embodiments of the positioning of biomaterial windows on a shaft of the fixation screw assembly.
Figure 9B:
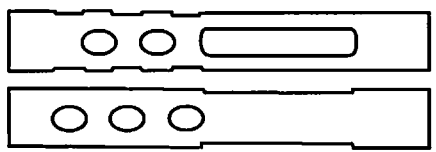
Figure 9C:
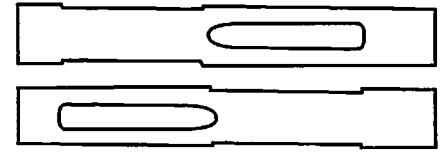
Figure 9D:
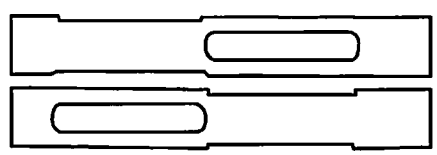
Figure 9E:
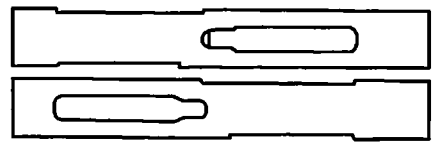

FIG. 8B illustrates yet another embodiment of the screw assembly 168. In this embodiment the shaft is provided with two biomaterial windows 170, 172. The first biomaterial window 170 is positioned closer to the screw head 174 and the second biomaterial window 172 is positioned closer to the distal end of the shaft 176. The first and second biomaterial windows are perpendicular to one another and overlap. The shaft of the screw assembly is also cannulated. FIGS. 9A-9E illustrate different configurations of the biomaterial windows on the shaft of screw assembly. FIG. 9A illustrates a shaft of screw assembly with three biomaterial windows, with two of the biomaterial windows in a first plane and a third biomaterial window offset by 90 degrees and configured to overlap with the first and second biomaterial windows. FIG. 9B illustrates an embodiment in the which the shaft of a screw assembly is provided with a one elongated biomaterial window and two smaller circular or oval windows in a first plane. This embodiment also provides three additional circular or oval windows offset by 90 degrees form the first plane and configured to overlap the two circular windows of the first plane. FIG. 9C illustrates a shaft of a screw assembly having a first bullet nosed biomaterial window in a first plane and a second bullet nosed biomaterial window in a second plane offset by 90 degrees. The first bullet nosed biomaterial window and the second bullet nosed biomaterial window are configured to overlap with one another. FIGS. 9D and 9E are additional embodiments of a shaft of a screw assembly with a first and second biomaterial window offset by 90 degrees and overlapping. More specifically, as illustrated in FIGS. 9A, 9C and 9E, the biomaterial windows may be tapered. It should be noted the biomaterial window may be formed in any shape that would allow bone growth.

The overlapping geometry of the biomaterial windows ensure that the fusion area will cross the joint regardless of insertion point or trajectory. The multiple fusion areas are intended to increase the chance of fusion along the length of the screw to decrease screw migration. This is advantageous to accommodate various patient anatomy, various bone quality, and various trajectories. The shaft of the screw assembly may also include several overlapping perpendicular slots intended to be filled with bone graft and cross either the sacroiliac joint for fusion or enhance fusion and prevent migration of the screw especially for longer screw lengths. The screw assemblies as illustrated in FIGS. 8A and 8B are also cannulated.

FIG. 10 illustrates a screw assembly that is configured with a laser engraving treatment. A nanotube treatment may be added to the screw to improve osseointegration and antimicrobial properties. The subtractive treatments may also be applied to the minor diameter of the threads as to not compromise structural integrity of the screw. The treatment may be offset from the sharp edges of the biomaterial windows to reduce the likelihood of crack propagation. The subtractive treatment may be applied along the entire length of the screw or only at the portion of the screw that comes in contact with sacral bone. The subtractive treatment may be omitted near the slotted portion of the screw.

FIGS. 11A-11F illustrates the screw assembly manufactures by various methods. Specifically, FIG. 11A illustrates the screw assembly is a machined assembled screw. FIG. 11B is an acid etched screw. FIG. 11C is a machined screw with laser engravings. FIG. 11D is a machined screw that includes 3D printed bone plugs positioned within the biomaterial windows. FIG. 11E is a 3D printed screw. FIG. 11F is a 3D printed dowel with 3D printed porous plug that is positioned within the biomaterial windows.

Methods

The fixation screw assemblies and/or lag screw assemblies described above can be used in various surgical methods, and in particular, those involving fusion of the sacroiliac joint. The screw assemblies can be inserted minimally invasively, and can be inserted using one or more percutaneous delivery instruments.

In some embodiments, the application encompasses surgical methods including:

a. forming an incision in a patient, wherein the incision has a width of between about 7 mm and 33 mm;

b. inserting a guide sleeve percutaneously through the incision to provide a lateral approach for inserting a fixation screw assembly;

c. inserting a fixation screw assembly through the guide sleeve, wherein the fixation screw assembly includes a flexible washer member and a bone engagement portion comprising a shaft and head portion, wherein the washer member is pre-assembled in a locked configuration around the head portion, and wherein the washer member is configured to move polyaxially relative to the shaft and head portion;

d. using a screw driver to drive the fixation screw assembly through an ilium, sacroiliac joint and sacrum;

e. driving the fixation screw assembly through the bone members until the washer member compresses against a surface of the ilium, thereby helping to prevent back out of the fixation screw;

f. maintaining the fixation screw in place to assist in fusion of the sacroiliac joint.

The process described above can be repeated multiple times until two, three or more fixation screw assemblies are deposited across the sacroiliac joint. Advantageously, in some embodiments, at least two fixation screw assemblies are provided to stabilize and assist in the fusion of the sacroiliac joint. In some embodiments, at least three fixation screw assemblies are provided, as shown in FIG. 6. As shown in the illustrated embodiment, the fixation screw assemblies 5a, 5b, and 5c can include bone engagement portions 8 having shafts 10 of variable lengths. For example, while fixation screw assemblies 5a and 5c have shafts 10 that are long enough to be implanted through a portion of an ilium 7, sacroiliac joint 11 and sacrum 9, fixation screw assembly 5b has a relatively shorter shaft that passes only through a portion of the ilium 7.

Figure 12A:
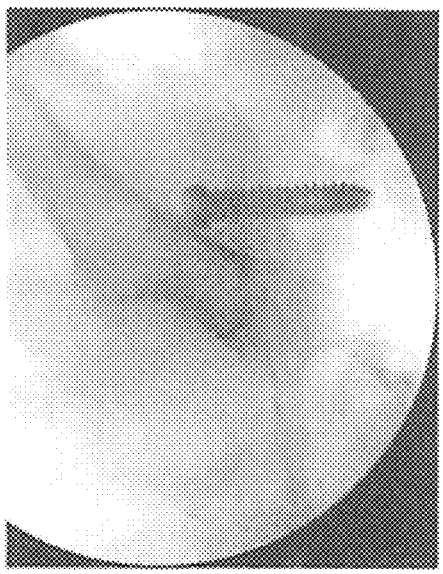
FIGS. 12A-12C illustrate the positioning of the screw assembly within the body using different methods.
Figure 12B:
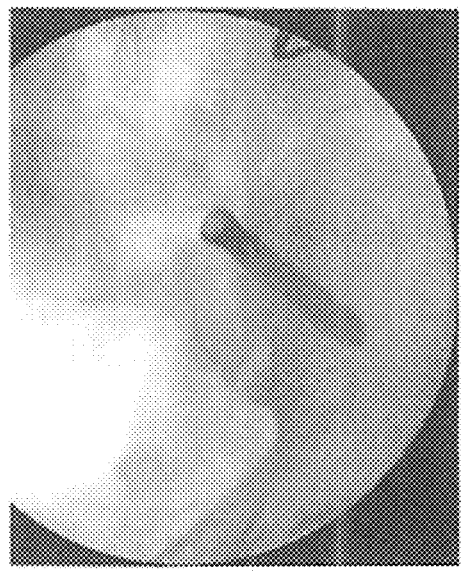
Figure 12C:
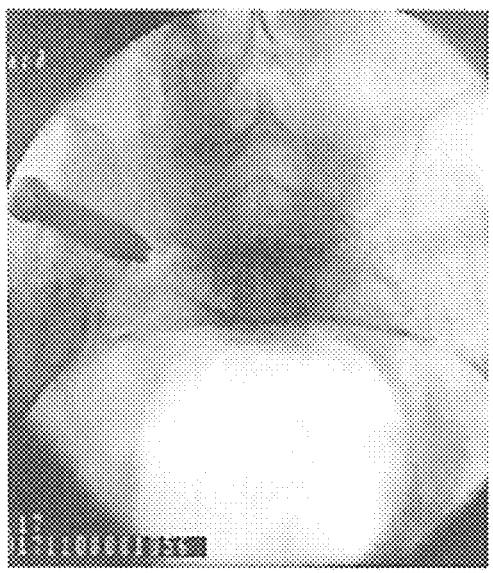

While the process detailed above describes a lateral approach, one skilled in the art will appreciate that insertion of the fixation screw assembly and/or lag screw assemblies can be performed via other approaches as well, including anteriorly and posteriorly. For instance, FIGS. 12A, 12B, and 12C illustrate different approaches for positioning the screw assembly. FIG. 12A illustrates a method in which the screw assembly is positioned in a lateral approach. FIG. 12B illustrates a method in which the screw assembly is positioned in a posterior approach placing the screw assembly medial to lateral and FIG. 12C illustrates a method in which the screw is positioned with a posterior approach placing the screw lateral to medial. In addition, the processes encompassed by this application are not limited to the steps described above. For example, an additional step can be provided in which biologic material is introduced into the fixation screw assembly (e.g., via a biomaterial window), thereby aiding in the fusion of the sacroiliac joint.

It will be apparent to those skilled in the art that various modifications and variations can be made in the present invention without departing from the scope or spirit of the invention. Moreover, the improved implants and related methods of use need not feature all of the objects, advantages, features and aspects discussed above. Thus, for example, those skilled in the art will recognize that the invention can be embodied or carried out in a manner that achieves or optimizes one advantage or a group of advantages as taught herein without necessarily achieving other objects or advantages as may be taught or suggested herein. In addition, while a number of variations of the invention have been shown and described in detail, other modifications and methods of use, which are within the scope of this invention, will be readily apparent to those of skill in the art based upon this disclosure. It is contemplated that various combinations or subcombinations of these specific features and aspects of embodiments may be made and still fall within the scope of the invention. Accordingly, it should be understood that various features and aspects of the disclosed embodiments can be combined with or substituted for one another in order to form varying modes of the discussed spacer implants. Thus, it is intended that the present invention cover the modifications and variations of this invention provided that they come within the scope of the appended claims or their equivalents.

What is claimed is:

1. A fixation screw assembly for fusing a sacroiliac joint comprising:
    a bone screw including a head and a shank coupled to the head to define a longitudinal axis of the bone screw, the head having a generally spherical outer surface defining an equator plane, the shank including a first biomaterial window and a second biomaterial window, the first biomaterial window and the second biomaterial window being circumferentially offset from each other and at least partially overlapping longitudinally;
    a washer disposed around the bone screw head, an inner surface of the washer being generally spherical and corresponding to the generally spherical outer surface of the head for polyaxial movement around the head relative to the longitudinal axis of the bone screw, wherein at least a portion of the washer is positioned below the equator plane at any polyaxial angle of the washer relative to the longitudinal axis of the bone screw,
    wherein when the washer is sufficiently angled relative to the longitudinal axis of the bone screw, a lip of the washer bottoms out on a groove of the head.
2. The screw assembly of claim 1, wherein the washer includes a plurality of teeth configured to directly engage the bone.
3. The assembly of claim 2, wherein the teeth are tapered inward to allow the teeth to recess into the bone.
4. The screw assembly of claim 1, wherein the first and second biomaterial windows are disposed circumferentially perpendicular to one another.
5. The assembly of claim 1, wherein the shank includes a third biomaterial window offset 90 degrees relative to the first biomaterial window.
6. The assembly of claim 1, wherein the bone screw is cannulated and has a cannulated opening at a proximal end of the shank, and the first and second biomaterial windows are each in fluid communication with the cannulated opening.
7. The assembly of claim 6, wherein the bone screw includes a dual inner diameter including a first portion with shallow threads and a second portion with deep threads.
8. The assembly of claim 1, wherein the bone screw is a 3D printed bone screw.
9. The assembly of claim 1, wherein the washer is configured to be angled, rotated or swiveled in multiple directions.
10. The assembly of claim 1, wherein the bone screw includes a dual inner diameter including a first portion with shallow threads and a second portion with deep threads.
11. A fixation screw assembly for fusing a sacroiliac joint comprising:
    a bone screw including a head and a shank including a plurality of threads coupled to the head to define a longitudinal axis of the bone screw, the head having a generally spherical outer surface defining an equator plane, the shank including a first biomaterial window and a second biomaterial window, the first biomaterial window and the second biomaterial window being circumferentially offset from each other and at least partially overlapping longitudinally, wherein the shank includes a dual inner diameter including a first portion with shallow threads and a second portion with deep threads; and
    a washer disposed around the head of the bone screw, an inner surface of the washer being generally spherical and corresponding to the generally spherical outer surface of the head for polyaxial movement relative to the longitudinal axis of the bone screw, wherein at least a portion of the washer is positioned below the equator plane at any polyaxial angle of the washer relative to the longitudinal axis of the bone screw,
    wherein when the washer is sufficiently angled relative to the longitudinal axis of the bone screw, a lip of the washer bottoms out on a groove of the head.
12. The assembly of claim 11, wherein the bone screw is cannulated with an opening extending from a proximal portion to a distal portion of the bone screw.
13. The assembly of claim 11, wherein the shank includes a third biomaterial window circumferentially offset 90 degrees relative to the second biomaterial window and overlaps the second biomaterial window longitudinally.
14. The assembly of claim 13, wherein the bone screw is cannulated and has a cannulated opening at a proximal end of the shank, and the first, second and third biomaterial windows are each in fluid communication with the cannulated opening.
15. The assembly of claim 11, wherein the groove is disposed at a proximal-most end of the head and the lip is disposed at a proximal-most end of the washer.
16. The assembly of claim 11, wherein the bone screw is a 3D printed bone screw.

17. The assembly of claim 11, wherein the washer is configured to be angled, rotated or swiveled in multiple directions.

18. The assembly of claim 11, wherein the washer includes one or more engagement surfaces configured to engage the bone.

19. The assembly of claim 18, wherein the engagement surfaces are teeth that are tapered inward to allow the teeth to recess into bone.

\* \* \* \* \*